United States Patent
Na et al.

(10) Patent No.: US 11,958,897 B2
(45) Date of Patent: Apr. 16, 2024

(54) ANTI-VAMP2 ANTIBODY FOR INHIBITING SNARE COMPLEX AND USE THEREOF

(71) Applicant: HAUUL BIO, Chuncheon-si (KR)

(72) Inventors: Hee-Jun Na, Chuncheon-si (KR);
Yun-Suk Lee, Chuncheon-si (KR);
Je-Ok Yoo, Chuncheon-si (KR);
Kwang-Soon Lee, Chuncheon-si (KR);
Kang Seung Lee, Chuncheon-si (KR);
Seung Je Min, Chuncheon-si (KR)

(73) Assignee: HAUUL BIO, Chuncheon-si (KR)

( * ) Notice: Subject to any disclaimer, the term of this patent is extended or adjusted under 35 U.S.C. 154(b) by 806 days.

(21) Appl. No.: 17/057,116

(22) PCT Filed: Aug. 14, 2019

(86) PCT No.: PCT/KR2019/010395
§ 371 (c)(1),
(2) Date: Nov. 20, 2020

(87) PCT Pub. No.: WO2020/040481
PCT Pub. Date: Feb. 27, 2020

(65) Prior Publication Data
US 2021/0198348 A1    Jul. 1, 2021

(30) Foreign Application Priority Data

Aug. 23, 2018  (KR) .................. 10-2018-0098309
Jun. 4, 2019   (KR) .................. 10-2019-0066179

(51) Int. Cl.
*C07K 16/18*   (2006.01)
*A61K 8/64*    (2006.01)

(52) U.S. Cl.
CPC .............. *C07K 16/18* (2013.01); *A61K 8/64* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2011/0112181 | A1 | 5/2011 | Kweon et al. |
| 2012/0107431 | A1 | 5/2012 | Kim et al. |
| 2018/0222878 | A1 | 8/2018 | Kweon et al. |
| 2019/0219575 | A1 | 7/2019 | Gray et al. |

FOREIGN PATENT DOCUMENTS

| | | |
|---|---|---|
| KR | 10-2011-0006290 A | 1/2011 |
| KR | 10-2017-0015845 A | 2/2017 |
| WO | 2008-111796 A1 | 9/2008 |
| WO | 2011-002179 A2 | 1/2011 |
| WO | 2018-073288 A1 | 4/2018 |

OTHER PUBLICATIONS

Rudikoff et al., Proc Natl Acad Sci USA 79(6): 1979-83 (Year: 1982).*
Piche-Nicholas et al., MABS 10(1): 81-94 (Year: 2018).*
Perera et al., J Neurology Neuromedicine 4(1): 35-40 (Year: 2019).*
International Search Report for PCT/KR2019/010395 dated Nov. 26, 2019 from Korean Intellectual Property Office.

* cited by examiner

*Primary Examiner* — Phuong Huynh
(74) *Attorney, Agent, or Firm* — Revolution IP, PLLC

(57) ABSTRACT

The present invention relates to an anti-VAMP2 antibody that inhibits SNARE complex and uses thereof, and more specifically, the present invention relates to an anti-VAMP2 antibody or antigen-binding fragments thereof comprising heavy and light chain CDRs of a specific sequence. The anti-VAMP2 antibody is expected to be useful for improving or treating skin wrinkles by inhibiting SNARE complex formation.

4 Claims, 5 Drawing Sheets
Specification includes a Sequence Listing.

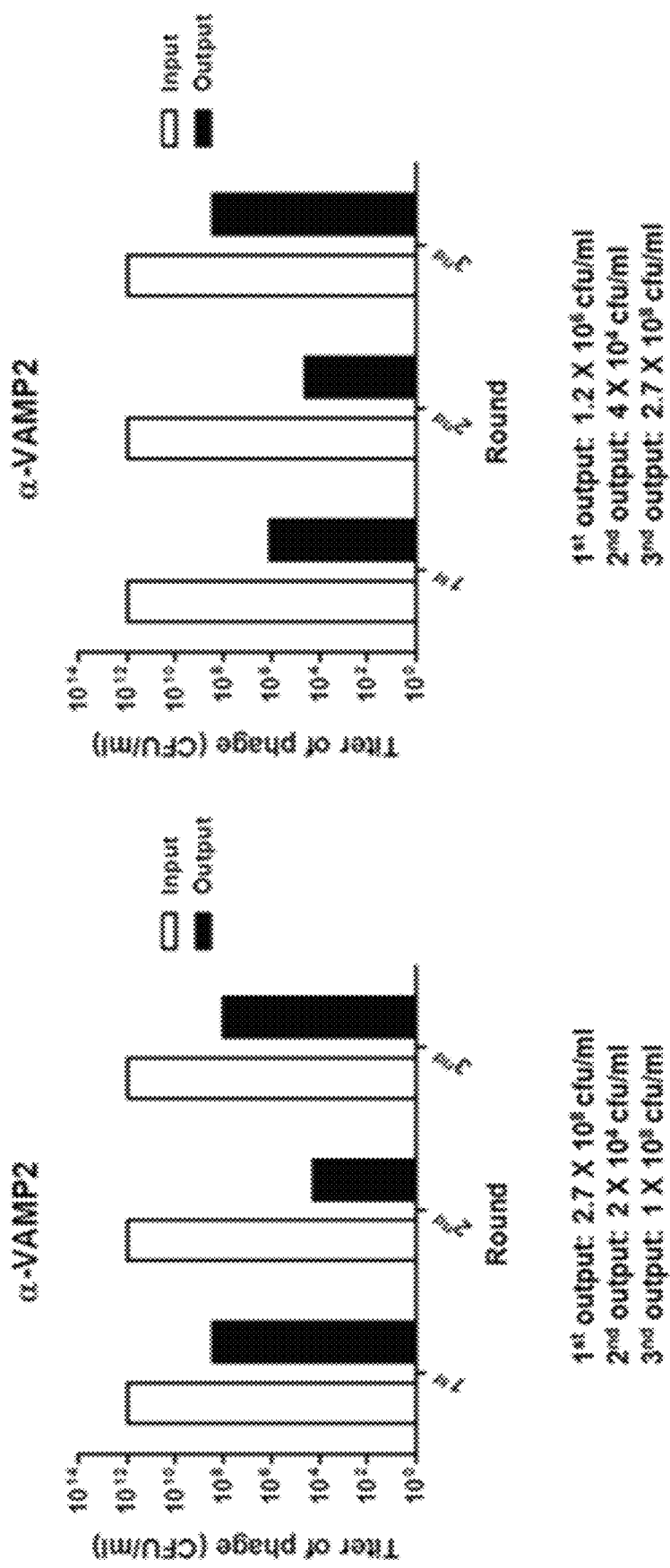
[FIG. 1]

[FIG. 2]
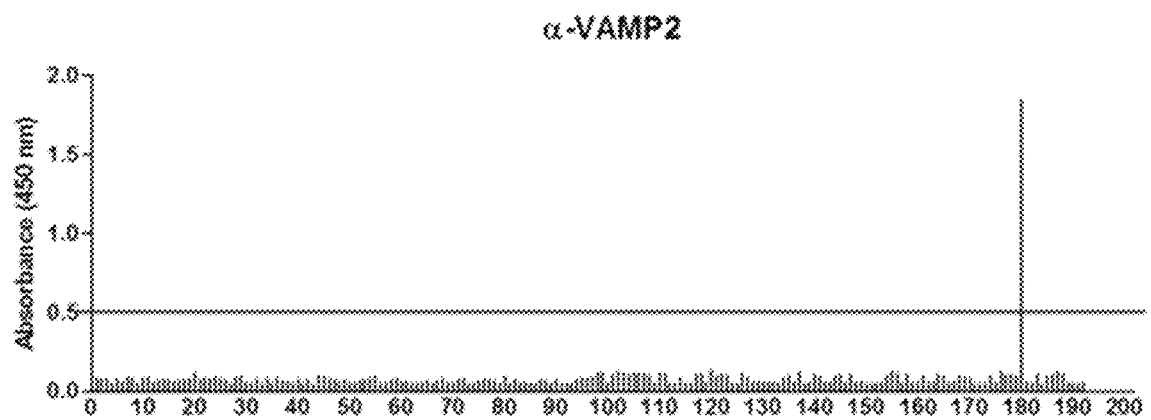
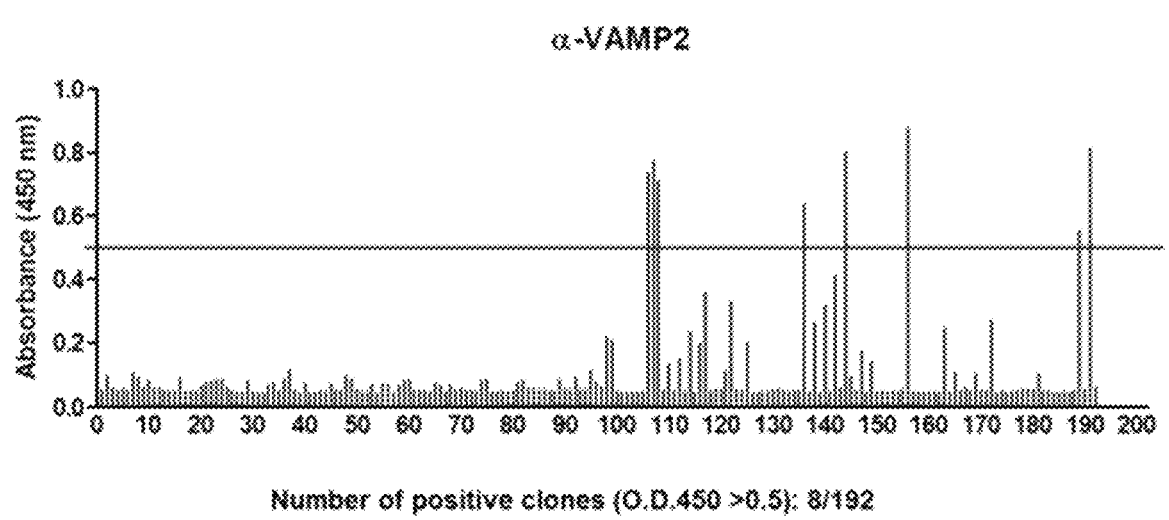

[FIG. 3]
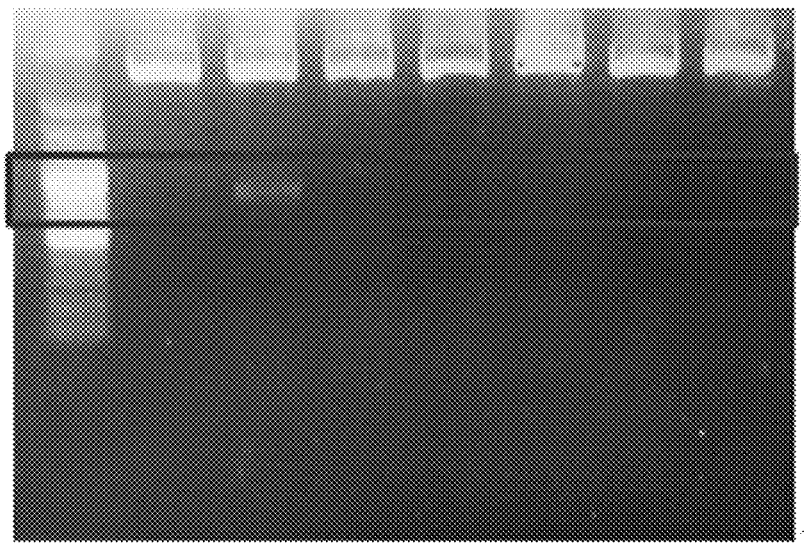
[FIG. 4]
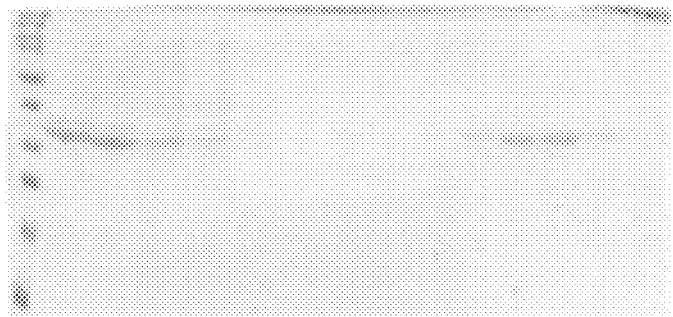
M : protein marker
T: Total cell lysate
P: Pellet
S: Supernatant
F: Flow through
L: lysis buffer
W1: Wash buffer (0.5% Triton X-100)
W2: Wash buffer (50 mM Imidazole)

[FIG. 5]
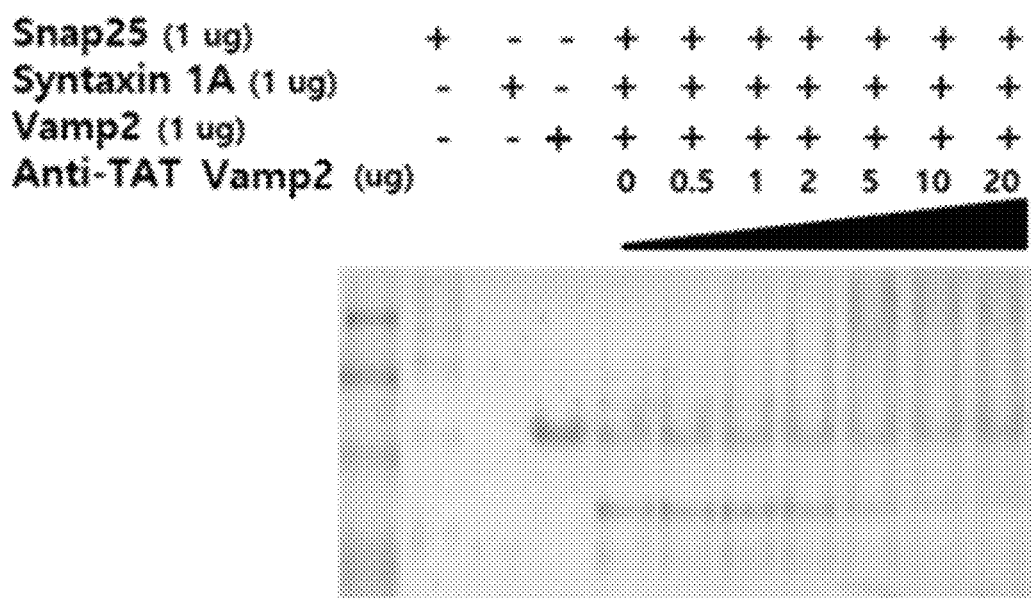
[FIG. 6]
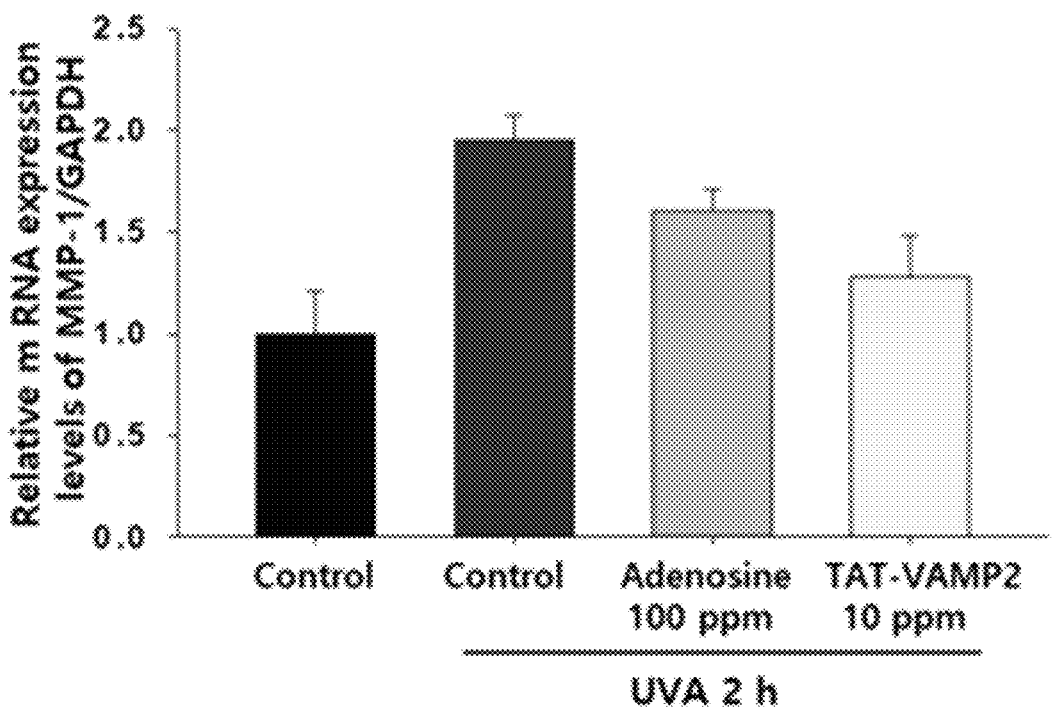

[FIG. 7]
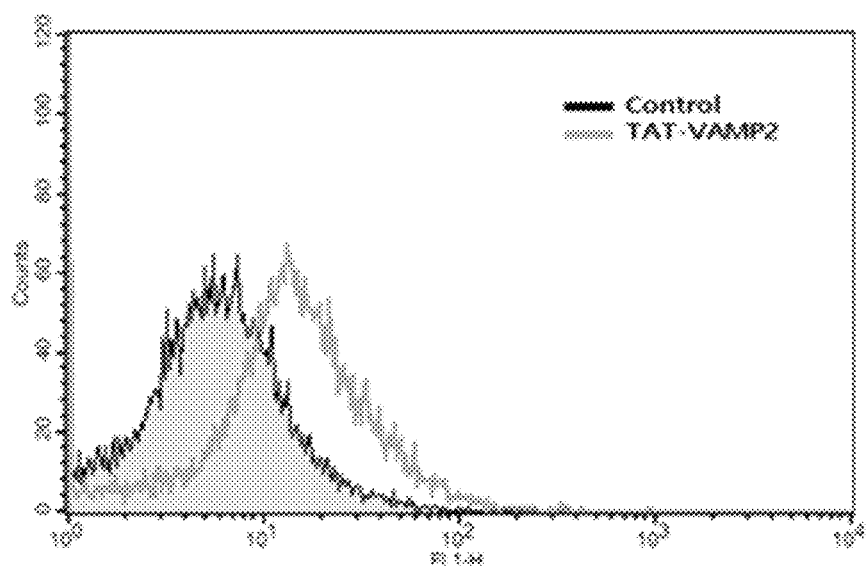

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: light chain CDR1

<400> SEQUENCE: 1

Thr Gly Ser Ser Ser Asn Ile Gly Ser Asn Asn Val Thr
1               5                   10

<210> SEQ ID NO 2
<211> LENGTH: 4
<212> TYPE: PRT
<213> ORGANISM: Artificial Sequence
<220> FEATURE:
<223> OTHER INFORMATION: light chain CDR2

<400> SEQUENCE: 2

Ser Asp Ser His
1

<210> SEQ ID NO 3
<211> LENGTH: 9
<212> TYPE: PRT
<213> ORGANISM: Artificial Sequence
<220> FEATURE:
<223> OTHER INFORMATION: light chain CDR3

<400> SEQUENCE: 3

Gly Ser Trp Asp Tyr Ser Leu Ser Ala
1               5

<210> SEQ ID NO 4
<211> LENGTH: 5
<212> TYPE: PRT
```

```
<213> ORGANISM: Artificial Sequence
<220> FEATURE:
<223> OTHER INFORMATION: heavy chain CDR1

<400> SEQUENCE: 4

Asn Tyr Ser Met Ser
1               5

<210> SEQ ID NO 5
<211> LENGTH: 9
<212> TYPE: PRT
<213> ORGANISM: Artificial Sequence
<220> FEATURE:
<223> OTHER INFORMATION: heavy chain CDR2

<400> SEQUENCE: 5

Ala Ile Tyr Ser Asp Gly Ser Ser Ile
1               5

<210> SEQ ID NO 6
<211> LENGTH: 19
<212> TYPE: PRT
<213> ORGANISM: Artificial Sequence
<220> FEATURE:
<223> OTHER INFORMATION: heavy chain CDR3

<400> SEQUENCE: 6

Lys Tyr Arg Ser Ser Lys His Thr Pro Leu Pro Ser Tyr Ser Asn Ala
1               5                   10                  15

Met Asp Val

<210> SEQ ID NO 7
<211> LENGTH: 11
<212> TYPE: PRT
<213> ORGANISM: Artificial Sequence
<220> FEATURE:
<223> OTHER INFORMATION: TAT peptide

<400> SEQUENCE: 7

Tyr Gly Arg Lys Lys Arg Arg Gln Arg Arg Arg
1               5                   10

<210> SEQ ID NO 8
<211> LENGTH: 33
<212> TYPE: DNA
<213> ORGANISM: Artificial Sequence
<220> FEATURE:
<223> OTHER INFORMATION: TAT peptide

<400> SEQUENCE: 8
tatggccgca aaaacgccgc ccagcgccgc cgc                               33

<210> SEQ ID NO 9
<211> LENGTH: 20
<212> TYPE: DNA
<213> ORGANISM: Artificial Sequence
<220> FEATURE:
<223> OTHER INFORMATION: Primer (MMP-1) - Forward

<400> SEQUENCE: 9
acgcagattt agcctccgaa                                              20

<210> SEQ ID NO 10
<211> LENGTH: 20
<212> TYPE: DNA
<213> ORGANISM: Artificial Sequence
```

```
<220> FEATURE:
<223> OTHER INFORMATION: Primer (MMP-1) - Reverse

<400> SEQUENCE: 10
tgacttggta atgggttgcc                                               20

<210> SEQ ID NO 11
<211> LENGTH: 20
<212> TYPE: DNA
<213> ORGANISM: Artificial Sequence
<220> FEATURE:
<223> OTHER INFORMATION: Primer (GAPDH) - Forward

<400> SEQUENCE: 11
gacatgccgc ctggagaaac                                               20

<210> SEQ ID NO 12
<211> LENGTH: 20
<212> TYPE: DNA
<213> ORGANISM: Artificial Sequence
<220> FEATURE:
<223> OTHER INFORMATION: Primer (GAPDH) - Reverse

<400> SEQUENCE: 12
agcccaggat gccctttagt                                               20
```

ANTI-VAMP2 ANTIBODY FOR INHIBITING SNARE COMPLEX AND USE THEREOF

CROSS REFERENCE TO PRIOR APPLICATIONS

This application is the 35 U.S.C. 371 national stage of International application PCT/KR2019/010395 filed on Aug. 14, 2019; which claims priority to Korean application 10-2018-0098309 filed on Aug. 23, 2018 and Korean application 10-2019-0066179 filed Jun. 4, 2019. The entire contents of each of the above-identified applications are hereby incorporated by reference.

TECHNICAL FIELD

The present invention relates to anti-VAMP2 antibodies that inhibit SNARE complexes and uses thereof.

BACKGROUND ART

Membrane fusion in cells is caused by proteins called soluble N-ethylmaleimide sensitive factor attachment protein receptor (SNARE). SNARE protein refers to a specific group of proteins that are very well preserved across all species, and SNARE complex refers to complexes of these proteins. SNARE protein can be divided into target (t-) SNARE and vesicular (v-) SNARE, and t-SNARE refers to the SNARE protein present in the presynaptic membrane and v-SNARE refers to the SNARE protein present in the synaptic vesicle. t-SNARE consists of an integral membrane protein called syntaxin 1a and a peripheral membrane protein, SNAP-25 (soluble NSF attachment protein of 25 kDa), and its functional unit is considered to be its complex (t-SNARE complex). v-SNARE refers to a membrane protein called vesicle-associated membrane protein 2 (VAMP2 or synaptobrevin). These SNARE proteins have a region of about 60 to 70 aa called 'SNARE core', and these regions gather together to form a four-helical bundle called SNARE complex.

Although studies related to the SNARE complex are actively underway, however studies on antibodies inhibiting the SNARE complex are still insufficient.

DISCLOSURE

Technical Problem

An object of the present invention is to provide an anti-VAMP2 antibody or antigen-binding fragment thereof that inhibits a SNARE complex.

Another object of the present invention is to provide a fusion anti-VAMP2 antibody or antigen-binding fragment thereof in which a TAT peptide is additionally bound to the anti-VAMP2 antibody or antigen-binding fragment thereof.

Another object of the present invention is to provide a nucleic acid molecule encoding the antibody or antigen-binding fragment thereof, a recombinant expression vector comprising the nucleic acid molecule, and cells transformed with the recombinant expression vector.

Another object of the present invention is to provide a composition for detecting VAMP2 antigen comprising the antibody or antigen-binding fragment thereof as an active ingredient.

Another object of the present invention is to provide a cosmetic composition for preventing or improving skin wrinkles, a health functional food composition, and a pharmaceutical composition for preventing or treating skin wrinkles comprising the antibody or antigen-binding fragment thereof as an active ingredient.

Technical Solution

To achieve the above object, the present invention provides an anti-VAMP2 antibody or antigen-binding fragment thereof comprising: a light chain variable region comprising a light chain CDR1 comprising an amino acid sequence represented by SEQ ID NO: 1, a light chain CDR2 comprising an amino acid sequence represented by SEQ ID NO: 2 and a light chain CDR3 comprising an amino acid sequence represented by SEQ ID NO: 3; and a heavy chain variable region comprising a heavy chain CDR1 comprising an amino acid sequence represented by SEQ ID NO: 4, a heavy chain CDR2 comprising an amino acid sequence represented by SEQ ID NO: 5, and a heavy chain CDR3 comprising an amino acid sequence represented by SEQ ID NO: 6.

Also, the present invention provides a fusion anti-VAMP2 antibody or antigen-binding fragment thereof in which TAT peptide represented by SEQ ID NO: 7 is additionally bound to the anti-VAMP2 antibody or antigen-binding fragment thereof.

In addition, the present invention provides a nucleic acid molecule encoding the antibody or antigen-binding fragment thereof.

In addition, the present invention provides a recombinant expression vector comprising the nucleic acid molecule.

In addition, the present invention provides cells transformed with the recombinant expression vector.

Furthermore, the present invention provides a composition for detecting VAMP2 antigen comprising the antibody or antigen-binding fragment thereof as an active ingredient.

In addition, the present invention provides a cosmetic composition for preventing or improving skin wrinkles comprising the antibody or antigen-binding fragment thereof as an active ingredient.

In addition, the present invention provides a health functional food composition for preventing or improving skin wrinkles comprising the antibody or antigen-binding fragment thereof as an active ingredient.

In addition, the present invention provides a pharmaceutical composition for preventing or treating skin wrinkles comprising the antibody or antigen-binding fragment thereof as an active ingredient.

Advantageous Effects

The present invention relates to an anti-VAMP2 antibody inhibiting a SNARE complex and uses thereof, and more particularly, the present invention relates to an anti-VAMP2 antibody or antigen-binding fragments thereof comprising heavy and light chain CDRs of a specific sequence. The anti-VAMP2 antibody is expected to be useful for improving or treating skin wrinkles by inhibiting SNARE complex formation.

DESCRIPTION OF DRAWINGS

FIG. 1 shows bio-panning results for the screening VAMP2 scFv antibody.

FIG. 2 shows results of ELISA analysis for screening VAMP2 scFv antibody.

FIG. 3 shows results of preparing a cell-permeable VAMP2 scFv through cloning.

FIG. 4 shows results of the size and the protein purity through SDS-PAGE after purification of the cell-permeable VAMP2 scFv protein.

FIG. 5 shows results of the native-PAGE analysis of the ability to inhibit SNARE complex formation of the cell-permeable VAMP2 scFv protein.

FIG. 6 shows results of inhibiting the MMP-1 collagenase activity of the cell-permeable VAMP2 scFv protein.

FIG. 7 shows results of flow cytometry of the cell permeability of the cell-permeable VAMP2 scFv protein.

BEST MODE

The present invention provides an anti-VAMP2 antibody or antigen-binding fragment thereof comprising: a light chain variable region comprising a light chain CDR1 comprising an amino acid sequence represented by SEQ ID NO: 1, a light chain CDR2 comprising an amino acid sequence represented by SEQ ID NO: 2 and a light chain CDR3 comprising an amino acid sequence represented by SEQ ID NO: 3; and a heavy chain variable region comprising a heavy chain CDR1 comprising an amino acid sequence represented by SEQ ID NO: 4, a heavy chain CDR2 comprising an amino acid sequence represented by SEQ ID NO: 5, and a heavy chain CDR3 comprising an amino acid sequence represented by SEQ ID NO: 6.

Also, the present invention provides a fusion anti-VAMP2 antibody or antigen-binding fragment thereof in which TAT peptide represented by SEQ ID NO: 7 is additionally bound to the anti-VAMP2 antibody or antigen-binding fragment thereof.

On the other hand, CDRs consisting of amino acids represented by SEQ ID NO: 1 to SEQ ID NO: 6 are listed in Table 1.

In addition, the amino acid sequence of the TAT peptide used in the present invention is "YGRKKRRQRRR" (SEQ ID NO: 7), and the nucleic acid sequence of the TAT peptide is

```
                                            (SEQ ID NO: 8)
"TAT GGC CGC AAA AAA CGC CGC CAG CGC CGC CGC".
```

In the present invention, the term, "antibody" refers to a protein molecule that serves as a receptor specifically recognizing an antigen, including an immunoglobulin molecule that is immunologically reactive with a specific antigen, for example, a monoclonal antibody, a polyclonal antibody, full-length antibody and antibody fragments. The term, "antibody" can also include bivalent or bispecific molecules (e.g., bispecific antibody), diabody, triabody or tetrabody.

In the present invention, the term "monoclonal antibody" refers to an antibody molecule of a single molecular composition obtained from a population of substantially the same antibody, which exhibits a single binding and affinity to a specific epitope, unlike polyclonal antibody which can bind multiple epitopes. In the present invention, the term, "full-length antibody" has two full-length light chains and two full-length heavy chains, of which each light chain is connected to a heavy chain through a disulfide bond. The constant region of the heavy chain has gamma (γ), mu (μ), alpha (α), delta (δ), and epsilon (ε) types, and its subclass has gamma 1 (γ1), gamma 2 (γ2), and gamma 3 (γ3)), gamma 4 (γ4), alpha 1 (α1) and alpha 2 (α2). The constant region of the light chain has kappa (κ) and lambda (λ) types. IgG is a subtype, and includes IgG1, IgG2, IgG3 and IgG4.

In the present invention, the term "heavy chain" refers to both a full-length heavy chain and fragments thereof comprising a variable region VH comprising an amino acid sequence having sufficient variable region sequences to confer specificity to the antigen and three constant regions CH1, CH2 and CH3. Further, in the present invention, the term "light chain" may include both a full-length light chain and fragments thereof comprising a variable region VL comprising an amino acid sequence having sufficient variable region sequences to confer specificity to the antigen and a constant region CL.

In the present invention, the terms "fragment", "antibody fragment" and "antigen-binding fragment" are used interchangeably to refer to any fragment of the antibody of the invention that has the antigen-binding function of the antibody. Exemplary antigen binding fragments include Fab, Fab', F(ab')2 and Fv, but they are not limited thereto.

Antibodies or antigen-binding fragments thereof of the present invention may include not only the sequences of the antibodies described herein, but also biological equivalents thereof, to the extent that they can exhibit the ability to specifically bind VAMP2. For example, additional changes may be made to the amino acid sequence of the antibody to further improve the binding affinity and/or other biological properties of the antibody, such modifications include, for example, deletion, insertion and/or substitution of amino acid sequence residues of the antibody. These amino acid variations are made based on the relative similarity of amino acid side chain substituents, such as hydrophobicity, hydrophilicity, charge, size, and the like. It can be seen by analyzing the size, shape and type of amino acid side chain substituents that arginine, lysine and histidine are all positively charged residues; alanine, glycine and serine have similar sizes; and phenylalanine, tryptophan and tyrosine have similar shapes. Therefore, based on the above, arginine, lysine and histidine; alanine, glycine and serine; and phenylalanine, tryptophan and tyrosine have biologically equivalent functions.

In addition, the present invention provides a nucleic acid molecule encoding the antibody or antigen-binding fragment thereof.

As used herein, the term "nucleic acid molecule" has the meaning of comprehensively including DNA (gDNA and cDNA) and RNA molecules, and nucleotides that are the basic structural units in nucleic acid molecules include not only natural nucleotides, but also analogues with modified sugar or base sites. The sequence of nucleic acid molecules encoding the heavy and light chain variable regions of the present invention can be modified, and the modifications include addition, deletion, or non-conservative substitutions or conservative substitutions of nucleotides.

In addition, the present invention provides a recombinant expression vector comprising the nucleic acid molecule.

In the present invention, "vector" refers to a self-replicating DNA molecule used to carry a clone gene (or other piece of clone DNA).

In the present invention, "expression vector" refers to a recombinant DNA molecule comprising a desired coding sequence and an appropriate nucleic acid sequence essential for expressing a coding sequence operably linked in a specific host organism. The expression vector may preferably include one or more selectable markers. The marker is a nucleic acid sequence having a property that can be selected by a chemical method, and all genes capable of distinguishing transformed cells from non-transformed cells are included. Examples include antibiotic-resistant genes such as ampicillin, kanamycin, geneticin (G418), bleomycin, hygromycin, chloramphenicol, etc., but they are not limited thereto, and can be appropriately selected by those skilled in the art.

To express the DNA sequence of the present invention, any of a wide variety of expression control sequences can be used in the vector. Examples of useful expression control sequences may include, for example, may construction known to control expression of genes and various other sequences and combinations thereof of early and late promoters of SV40 or adenovirus, promoters and enhancers of CMV, retroviral LTR, lac system, trp system, TAC or TRC system, T3 and T7 promoters, a major operator and promoter region of phage lambda, a regulatory region of fd code protein, a promoter for 3-phosphoglycerate kinase or other glycolase, promoters of the phosphatase, e.g. Pho5, promoters of yeast alpha-hybridization system and prokaryotic or eukaryotic cells or viruses thereof.

The vector expressing the antibody of the present invention may be a vector system in which the light and heavy chains are simultaneously expressed in one vector, or a system in which the light and heavy chains are respectively expressed in separate vectors. In the latter case, both vectors are introduced into the host cell through co-transformation and targeted transformation. The co-transformation is a method of screening cells expressing both light and heavy chains after simultaneously introducing each vector DNA encoding light and heavy chains into a host cell. The targeted transformation is a method of selecting cells transformed with a vector containing a light chain (or heavy chain) and again transforming the selected cells expressing the light chain with a vector containing a heavy chain (or light chain) to express both the light and heavy chains, and thereby finally selecting cells.

In addition, the present invention provides cells transformed with a recombinant expression vector.

Cells capable of continuously cloning and expressing the vector of the present invention stably may be any host cell known in the art, may include prokaryotic host cells, for example, *Escherichia coli*, *Bacillus* strains such as *Bacillus subtilis* and *Bacillus thuringiensis*, *Streptomyces*, *Pseudomonas* (e.g. *Pseudomonas putida*), *Proteus mirabilis* or *Staphylococcus* (e.g. *Staphylococcus carnosus*), but they are not limited thereto.

In the method of preparing the antibody or antigen-binding fragment thereof, the culture of transformed cells may be performed according to a suitable medium and culture conditions known in the art. Such a culture process can be performed by easily adjusting according to the selected strain by those skilled in the art. The cell culture is divided into a suspension culture and an adhesion culture according to the cell growth way and it is divided into batch, fed-batch and continuous culture methods depending on the culture method. The medium used for culture must adequately satisfy the requirements of a particular strain.

In addition, the present invention provides a composition for detecting VAMP2 antigen comprising the antibody or antigen-binding fragment thereof as an active ingredient.

In addition, the present invention provides a cosmetic composition for preventing or improving skin wrinkles comprising the antibody or antigen-binding fragment thereof as an active ingredient. Specifically, the composition can inhibit SNARE complex formation.

The cosmetic composition may include a stabilizing agent, a solubilizing agent, conventional adjuvants such as vitamins, pigments and fragrances, and a carrier, in addition to the active ingredient.

The formulation of the cosmetic composition may be prepared in any formulation conventionally prepared in the art, and may be a formulation selected from the group consisting of external skin ointment, cream, softening lotion, nutrient lotion, pack, essence, hair tonic, shampoo, rinse, hair conditioner, hair treatment, gel, skin lotion, skin softener, skin toner, astringent, lotion, milk lotion, moisture lotion, nutrition lotion, massage cream, nutrition cream, eye cream, moisture cream, hand cream, foundation, nutrition essence, sunscreen, soap, cleansing foam, cleansing lotion, cleansing cream, body lotion and body cleanser, but it is not limited thereto. The composition of each of these formulations may contain various bases and additives necessary and appropriate for the preparation of the formulation, and the types and amounts of these components can be easily selected by those skilled in the art.

When the formulation is paste, cream or gel, it may use animal oil, vegetable oil, wax, paraffin, starch, tragacanth, cellulose derivative, polyethylene glycol, silicone, bentonite, silica, talc or zinc oxide and the like, as the carrier component.

When the formulation is powder or spray, it may use lactose, talc, silica, aluminum hydroxide, calcium silicate or polyamide powder, as the carrier component, and in particular, the spray may additionally include a propellant such as chlorofluorohydrocarbon, propane/butane or dimethyl ether.

When the formulation is solution or emulsion, solvent, solubilizer or emulsifying agent are used as the carrier component, for examples water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid esters of sorbitan.

When the formulation is suspension, it may use liquid diluents such as water, ethanol or propylene glycol, suspending agents such as ethoxylated isostearyl alcohol, polyoxyethylene sorbitol esters, and polyoxyethylene sorbitan esters, microcrystalline cellulose, aluminum metahydroxide, bentonite, agar or tragacanth, as the carrier component.

In addition, the present invention provides a health functional food composition for preventing or improving skin wrinkles comprising the antibody or antigen-binding fragment thereof as an active ingredient. Specifically, the composition can inhibit SNARE complex formation.

The health functional food composition may be provided in the form of a powder, granule, tablet, capsule, syrup, beverage or pill, and the health food composition is used in combination with other food or food additives other than the composition according to the present invention as an active ingredient, and it can be suitably used according to the conventional method. The mixed amount of the active ingredient can be appropriately determined according to its purpose of use, for example, prevention, health or therapeutic treatment.

The effective dose of the antibody or antigen-binding fragments thereof contained in the health functional food composition can be used in accordance with the effective dose of the pharmaceutical composition, but it may be the above range and less than in the case of the long-term intake for health and hygiene purposes or for health control purposes and it is clear that the active ingredient can be used in an amount of at least the above range because there is no problem in terms of safety.

There is no particular limitation regarding the kind of the health functional food, and examples thereof include meat, sausage, bread, chocolate, candies, snacks, confectionery, pizza, ramen, other noodles, gums, dairy products including ice cream, various soups, beverages, tea, drinks, alcoholic beverages and vitamins complex, etc.

In addition, the present invention provides a pharmaceutical composition for preventing or treating skin wrinkles comprising the antibody or antigen-binding fragment thereof as an active ingredient. Specifically, the composition can inhibit SNARE complex formation.

The pharmaceutical composition of the present invention may further include a pharmaceutically acceptable carrier, and the pharmaceutically acceptable carrier is commonly used in the preparation and may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, stearic acid, magnesium and mineral oil, and the like, but it is not limited thereto. The pharmaceutical composition of the present invention may further include a lubricant, a wetting agent, a sweetener, a flavoring agent, an emulsifying agent, a suspending agent, a preservative, etc. in addition to the above components.

The pharmaceutical composition of the present invention can be administered orally or parenterally, and for parenteral administration, it can be administered by intravenous injection, subcutaneous injection, intramuscular injection, intraperitoneal injection, endothelial administration, topical administration, intranasal administration, intrapulmonary administration, rectal administration, etc. When administered orally, the protein or peptide is digested, so the composition for oral administration can be formulated to coat the active agent or to protect it from the degradation in the stomach, and the composition of the present invention can be administered by any device capable of transporting the active substance to target cells.

Suitable dosages of the pharmaceutical composition of the invention varies according to factors such as formulation method, mode of administration, patient's age, weight, sex, morbid condition, food, time of administration, route of administration, rate of excretion and response sensitivity, and usually, an experienced physician can easily determine and prescribe a dose effective for the desired treatment or prevention.

The pharmaceutical composition of the present invention is prepared in a unit dosage form by formulating using a pharmaceutically acceptable carrier and/or excipient or by incorporating it into a multi-dose container, according to a method that can be easily carried out by a person skilled in the art to which the present invention pertains. At this time, the formulation may be in the form of a solution, suspension, or emulsion in an oil or aqueous medium, or may be in the form of extract, powder, suppository, powder, granule, tablet or capsule, and may further include a dispersant or stabilizer.

The composition of the present invention may be administered as an individual therapeutic agent or in combination with other therapeutic agents and may be administered sequentially or simultaneously with conventional therapeutic agents.

Hereinafter, examples of the present invention will be described in detail to understand the present invention. The present invention may, however, be embodied in many different forms and should not be limited to the embodiments set forth herein in order to clearly illustrate the present invention for those skilled in the art to which the present invention pertains.

<Example 1> VAMP2 scFv Antibody Screening

1. Bio-Panning

Bio-panning was performed using an OPAL library with a diversity of $7.6 \times 10^9$. vamp2 antigen of 4 μg was immobilized on the epoxy magnetic bead and the input phage was reacted. The output titer was measured by elution of the phage reacted with the antigen. The input and output titers were measured every number of times to obtain bio-panning information and to confirm that it was running normally. For each number of times, an input phage $4 \times 10^{12}$ cfu/ml of phage was used. The results of sequential panning up to the 1st, 2nd and 3rd round were shown in FIG. 1. Outputs of $1 \times 10^8$ cfu/ml and $2.7 \times 10^8$ cfu/ml of VAMP2 were obtained, respectively (FIG. 1). Therefore, it was confirmed that bio-panning was performed normally.

2. ELISA Analysis

ELISA analysis was performed to screen antibodies having high sensitivity and high specificity. The obtained phage was infected with *E. coli* and streaked on LB plate to which antibiotics were added. After incubation in an incubator at 30° C. for 16 hours, the resulting colonies were randomly collected. After each colony was cultured in LB medium, it was treated with IPTG to express scFv, and *E. coli* was lysed to perform ELISA of a soluble fraction. First, 1 μg/ml of VAMP2 recombinant protein was each fixed in a 96 well ELISA plate and blocked with PBS containing 1% BSA. After 1 hour, the cell lysate obtained above was treated and reacted at 4° C. for 16 hours. After washing the plate three times with PBS containing 0.1% Tween20, the HRP conjugated anti-HA antibody was diluted in 1:1000 in a blocking solution and reacted at room temperature for 1 hour. The plate was washed 5 times with PBS containing 0.1% Tween20, and then colored with a TMB substrate to measure scFv antibody bound to the antigen by an ELISA leader. FIG. 2 shows the results of ELISA using VAMP2. 192 antibodies were analyzed, and one positive clone was obtained by arbitrarily determining OD 0.5 as a positive guideline and OD 0.1 as a negative guideline. In addition, it was repeatedly performed using 192 other colonies, and a total of 9 clones were selected (FIG. 2).

<Example 2> VAMP2 scFv Antibody Sequence Analysis

Individual clones were selected through sequencing for 9 positive clones of VAMP2 selected by ELISA analysis. Sequencing was necessary because there is a possibility that duplicate clones exist among the positive clones previously selected. As a result of the sequence analysis, it was confirmed that all nine of VAMP2 were the same clone (Table 1).

TABLE 1

| | | CDR1 | CDR2 | CDR3 | | CDR1 | CDR2 | CDR3 |
|---|---|---|---|---|---|---|---|---|
| VAMP1 | L | TGSSSNIGSNNVT | SDSH | GSWDYSLSA | H | NYSMS | AIYSDGSSI | KYRSSKHTPLPSYSNAMDV |
| | | SEQ ID NO: 1 | SEQ ID NO: 2 | SEQ ID NO: 3 | | SEQ ID NO: 4 | SEQ ID NO: 5 | SEQ ID NO: 6 |

\<Example 3\> Preparation of Cell-Permeable Anti-VAMP2 scFv

1. Preparation of TAT-VAMP2 scFv Construct

A PCR product in which a restriction enzyme site and a TAT were inserted was produced by using one of the previously selected scFvs as a primer. 30 µl of each PCR product was treated with 4 µl of buffer 3.1, 1 µl of Sal1, 1 µl of Xho1 and 4 µl of distilled water, reacted at 37° C. for 1 hour, and then DNA was separated to obtain an insert to be inserted into the vector. The pET28a(+) vector was transformed into DH5a competent cells, and then streaked on LB plates to which kanamycin was added, incubated at 37° C. for 16 hours, and next day, colonies were taken to inoculate in LB media to which kanamycin was added, and cultured at 37° C. for 16 hours. The next day, the vector is separated using a mini-prep kit, and 30 µl of the vector is treated with 4 µl of buffer 3.1, 1 µl of Sal1, 1 µl of Xho1, 1 µl of CIP and 3 µl of distilled water to react for 1 hour at 37° C. followed by purification. The concentration of the purified vector and inset was measured by nanodrop, and ligation was performed at room temperature for 16 hours using T4 ligase according to the ratio of vector and insert. After finishing the ligation, it was transformed to DH5a, streaked on a kanamycin-added LB plate, incubated at 37° C. for 16 hours, and the next day, colonies were taken to inoculate in a kanamycin-added LB media and incubated at 37° C. for 16 hours. The next day, to confirm the insertion of the insert, the plasmid was separated and cut with Sal1 and Xho1, and the band was confirmed by electrophoresis on a 1% agarose gel (FIG. 3).

2. TAT-VAMP2 scFv Antibody Purification

The cloned TAT-VAMP2 scFv antibody clone was transformed into a BL21(DE3) *E. coli* host, and the transformant was induced with 1 mM of IPTG. The scFv antibody was suspended in a lysis buffer (50 mM Tris-HCl, pH 7.5, 150 mM NaCl), pulverized using an ultrasonicator and centrifuged to obtain a supernatant. Purification of the protein was performed using a resin having affinity for Ni-NTA. The purified protein was confirmed to have a protein size of about 30 kDa through SDS-PAGE analysis (FIG. 4).

\<Example 4\> Cytotoxicity Test of Cell Permeable Anti-VAMP2 scFv

To examine the cytotoxicity of the TAT-VAMP2 scFv antibody, PC12 cells, mammalian neurons, were cultured in a 37° C. in a $CO_2$ incubator. After the culture, each of the TAT-VAMP2 scFv antibodies was treated by concentration (0.1, 1, 10, 50, 100, 200, 400 ppm) and further cultured under the same culture conditions. After culturing, MTT{3-(4,5-dimethylthiazol-2-yl)-2,5-diphenyltetrazolium bromide} solution was added and incubated, and then the culture solution was removed, DMSO (dimethyl sulfoxide) was added to shake appropriately, and absorbance was measured with an ELISA Reader system at 570 nm, and the values were shown in Table 2. As shown in Table 2, when the TAT-VAMP2 scFv was treated at concentrations of 0.1, 1, 10, 50, 100, 200, 400 ppm, it was confirmed that there was almost no change in cell shape and cell viability of mammalian neurons to the concentration of 400 ppm. Therefore, it was found that the TAT-VAMP2 scFv is a substance without cytotoxicity up to a concentration of 400 ppm.

TABLE 2

| Concentration (ppm) | TAT-VAMP2 scFv |
|---|---|
| 0 | 100% |
| 0.1 | 92.9 ± 6.5% |
| 1 | 106.6 ± 9.0% |
| 10 | 120.2 ± 2.0% |
| 50 | 133.4 ± 5.9% |
| 100 | 116.8 ± 3.1% |
| 200 | 137.5 ± 6.3% |
| 400 | 143.0 ± 5.3% |

\<Example 5\> Cell Permeable Anti-VAMP2 scFv SNARE Complex Formation Inhibition Ability Test To confirm whether TAT-VAMP2 scFv antibody inhibited SNARE complex formation, native-PAGE analysis was performed. When the SNARE proteins SNAP25, Syntaxin 1A and VAMP2 protein (LSbio Co.) were mixed at a concentration of 1:1:1 (1 µg), it was confirmed that the complex formed was inhibited by the addition of the TAT-VAMP2 scFv antibody. 1 µl of each protein was added, and each of the TAT-VAMP2 scFv antibodies was treated by concentration (0.5, 1, 2, 5, 10, 20 µg), mixed quickly using vortex, and reacted at 4° C. for 1 hour. When the reaction was completed, the sample buffer solution was added to stop the reaction, and it was confirmed whether SNARE complex was formed on 10% native-PAGE (FIG. 5). As shown in FIG. 5, TAT-VAMP2 scFv effectively inhibited the SNARE complex in a concentration-dependent manner (5, 10, 20 µg), and TAT-VAMP2 scFv inhibited SNARE complex formation by 50% at a concentration of 5 µg.

\<Example 6\> Evaluation of MMP-1 Expression Inhibition of Cell permeable anti-VAMP2 scFv To investigate the effect on collagen production for TAT-VAMP2 scFv, the effect of inhibiting MMP-1 activity by TAT-VAMP2 scFv was tested using Real Time PCR method. Mammalian neurons, PC12 cells, were cultured in a 37° C. in a $CO_2$ incubator. After incubation, UVA was irradiated using a UV irradiator system. Thereafter, 10 ppm of the TAT-VAMP2 scFv antibody and 100 ppm of adenosine as a positive control were used for treating and further cultured under the same culture conditions. After incubation, cells are collected with TRIzol 300 ul, transferred to a 1.5 ml tube, and 50 µl of chloroform is added and vortexed and left at room temperature for 5 minutes. Subsequently, the supernatant was transferred to a new tube by centrifugation at 4° C. and 15,000 rpm for 15 minutes, mixed with the same amount of 2-propanol, and allowed to stand at room temperature for 5 minutes, followed by centrifugation at 4° C. and 12,000 rpm for 20 minutes. After centrifugation, 2-propanol was discarded, and 300 ul of 75% ethanol was added, followed by centrifugation at 4° C. and 10,000 rpm for 10 minutes, 75% ethanol was discarded, and the RNA pellet was dried at room temperature to remove the remaining ethanol. 30 µl of DEPC-treated purified water was added to the pellet to dissolve and quantified at 260 nm. 1 µg of total RNA was used for RT-PCR and TOPscript RT dry mix was used for RT-PCR. MMP-1 and GAPDH used in Real Time PCR were synthesized and used in Macrogen, and the nucleic acid sequences are shown in Table 3 below. Real Time PCR was performed using TOPreal™ Qpcr 2X Pre-MIX. As shown in FIG. 6, TAT-VAMP2 scFv inhibited MMP-1 collagenase, which causes wrinkle formation by ultraviolet rays. It was confirmed that the wrinkle improvement effect was superior to that of the control when treated with 10 ppm.

TABLE 3

| Primer | | Sequence | |
|---|---|---|---|
| MMP-1 | Forward | 5'-ACGCAGATTTAGCCTCCGAA-3' | (SEQ ID NO: 9) |
| | Reverse | 5'-TGACTTGGTAATGGGTTGCC-3' | (SEQ ID NO: 10) |
| GAPDH | Forward | 5'-GACATGCCGCCTGGAGAAAC-3' | (SEQ ID NO: 11) |
| | Reverse | 5'-AGCCCAGGATGCCCTTTAGT-3' | (SEQ ID NO: 12) |

<Example 7> Cell Permeability Measurement of Cell Permeable Anti-VAMP2 scFv

To confirm the cell permeation activity of TAT-VAMP2 scFv, the cell permeation activity was confirmed using PC12 cells, which are mammalian neurons. PC-12 cells were cultured for 24 hours using RPMI-1640 media containing 10% FBS and 1% penicillin/streptomycin in a 6 well plate ($1 \times 10^6$ cells/well). The cultured cells were washed twice with PBS, and the samples were treated in a serum-free medium without FBS for 3 hours (treatment concentration 50 ug). After the reaction time, the residual sample was removed by washing twice with PBS, and cells were collected in the prepared tube using 0.05% trypsin-EDTA. The recovered cells were washed 3 times with PBS, centrifuged at 1,500 rpm for 3 minutes, and then 3 ml of 70% cold EtOH was added and reacted for 1 hour. After washing 3 times with PBS, blocking was performed using 3% BSA, and staining was performed at room temperature for 30 minutes in a shaded state using His-probe FITC-conjugated. After the reaction, the staining solution was removed and washed three times with PBS. After removing the supernatant, 300 ul of PBS was added to each FACS tube, and then the cells were sufficiently resuspended to determine the permeation degree of TAT-VAMP2 scFv into the cells using FACSCalibur and FL-1 (488 nm). As shown in FIG. 7, it was found that TAT-VAMP2 scFv itself has excellent intracellular permeation activity.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. An anti-VAMP2 antibody or antigen-binding fragment thereof comprising:

a light chain variable region comprising a light chain CDR1 comprising the amino acid sequence of SEQ ID NO: 1, a light chain CDR2 comprising the amino acid sequence of SEQ ID NO: 2 and a light chain CDR3 comprising the amino acid sequence of SEQ ID NO: 3; and a heavy chain variable region comprising a heavy chain CDR1 comprising the amino acid sequence of SEQ ID NO: 4, a heavy chain CDR2 comprising the amino acid sequence of SEQ ID NO: 5, and a heavy chain CDR3 comprising the amino acid sequence of SEQ ID NO: 6.

2. A fusion protein, comprising:
a TAT peptide as set forth in SEQ ID NO: 7 fused to the anti-VAMP2 antibody or antigen-binding fragment thereof of claim 1.

3. A method of inhibiting SNARE complex formation, comprising:
contacting a cell with a composition comprising the anti-VAMP2 antibody or antigen-binding fragment thereof of claim 1, thereby inhibiting the SNARE complex formation in the cell.

4. A method of inhibiting MMP-1 activity mediated by ultraviolet rays, comprising:
contacting a cell with a composition comprising said fusion protein of claim 2, thereby inhibiting MMP-1 activity in the cell.

* * * * *